United States Patent [19]

Tam

[11] Patent Number: 5,741,647
[45] Date of Patent: Apr. 21, 1998

[54] FLOW THROUGH NUCLEIC ACID HYBRIDISATION USES THEREOF AND A DEVICE THEREOF

[76] Inventor: Joseph Wing On Tam, 25A Fu Chak Yuen, Block 18 Chi Fu Fa Yuen, 18 Chi Fu Road, Hong Kong, Hong Kong

[21] Appl. No.: 602,903

[22] Filed: Feb. 16, 1996

[51] Int. Cl.$^6$ .................................................. C12Q 1/68
[52] U.S. Cl. ........................... 435/6; 436/177; 436/807; 536/24.3; 935/77; 935/78
[58] Field of Search .................. 435/6; 436/177, 436/807; 536/24.3; 935/77.78

[56] References Cited

U.S. PATENT DOCUMENTS

| | | | |
|---|---|---|---|
| 4,366,241 | 12/1982 | Tom et al. | 435/7 |
| 4,727,019 | 2/1988 | Valkirs et al. | 435/5 |
| 4,818,677 | 4/1989 | Hay-Kaufman et al. | 435/4 |
| 4,824,776 | 4/1989 | Heller | 435/6 |
| 4,828,986 | 5/1989 | Smith et al. | 435/7 |
| 4,832,814 | 5/1989 | Root | 204/299 R |
| 4,835,100 | 5/1989 | Dixon et al. | 435/7 |
| 5,155,049 | 10/1992 | Kauvar et al. | 436/177 |
| 5,466,603 | 11/1995 | Meehan et al. | 435/285.1 |

FOREIGN PATENT DOCUMENTS 605 828 A1 7/1994 European Pat. Off. ................ 435/6

OTHER PUBLICATIONS

Saiki et al., Proc. Natl. Acad. Sci. (U.S.A) 86:6230–6234 1989.
Jones et al., Analytical Biochemistry 181:23–27 1989.

*Primary Examiner*—W. Gary Jones
*Assistant Examiner*—Paul B. Tran
*Attorney, Agent, or Firm*—Albert Wai-Kit Chan

[57] ABSTRACT

This invention provides methods for determining whether a target nucleic acid sequence is present in a sample and methods for determining the amount of a target nucleic acid sequence present in a sample using flow-through hybridisation technology. This invention also provides different embodiments of these methods. Finally, this invention also provides devices where these methods are carried out.

14 Claims, 8 Drawing Sheets

FLOW THROUGH NUCLEIC ACID HYBRIDISATION USES THEREOF AND A DEVICE THEREOF

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

DNA hybridisation has been the most essential method for research in modern biological science involving the molecular studies of genes. The complexity of nucleic acid sequences of various genomes were revealed by solution hybridisation through the annealing process of the complementarity of specific DNA sequences. The annealing kinetics (Britten and Kohne, 1968) in solution of the complementary single strand DNA in solution is dependent upon the bimolecular collision. Thus the rate of reaction is directly controlled by the diffusion rate and the concentration of the nucleic acid target sequence. Although quantitative estimation of a single unique sequence by solution hybridisation has been very satisfactory, this technique can not be used for the study of multiple sequences in mixture unless elaborate separation process is done. This difficulty was eliminated by the discovery of membrane hybridisation techniques first developed by Southern (Southern E. M. 1975). The DNA in question was first digested with restriction endonucleases, sized by agarose gel electrophoresis and then immobilized onto a nitrocellulose membrane. The specific DNA sequence was identified by hybridisation with radioactively labelled complementary DNA probe. Since the same membrane can be used for reprobing through multiple repeat hybridisations with probes of different segment sequences, the genomic organisation of a specific gene or gene family can be obtained. Similar experiments can also be performed to gain further information on other sequences in the same membrane. The applicant and collaborators used allele specific oligonucleotide(ASO) to detect the point mutations of the Chinese population in Hong Kong (Antonarakis, S. E. et al., 1988). Thus the Southern Blotting analysis has been the most widely used molecular biology technique to date. In the so call ZOO BLOT (Miller J. R and Koopman M, 1990), in which a panel of Southern Blots consisting DNA from different sources, mapped with different restriction endonucleases and target DNA probes, one can establish the existence as well as the location of homologous sequences of a wide variety of spices within single membrane. If one simply want to know the existence of certain sequence, e.g. neither the size nor the genomic details, the dot and slot blot analysis can provide rapid screening procedure for a large number of samples. Unfortunately neither the Southern nor the dot or slot blot methods can be extended to the study of multiple sequences simultaneously within the same membrane in a single run e.g. without the time consuming procedures of repeat hybridisation by different probes. Furthermore the available membranes presently on the market for blotting analysis are generally unable to provide high affinity binding to small molecular weight polynucleotide fragments of less than 100 bp. The use of direct gel hybridisation reported by us (Huang C. H. et al., 1988) removed the blotting process thereby reduced the procedural time considerably. However DNA fragments of smaller than 300 bp are still not detectable. The reversed dot blot technique advanced by Maggio, A. et al (1993) provided the solution to these problems. In this method the a large number of capture oligonucleotides (20–24 nt), used to capture the target DNA molecules, are covalently immobilized onto the Biodyne C membrane followed by hybridisation with the test sample(s) and colour development. With this immobilisation techniques the number of capture nucleotide is in principle limited only by the area of the membrane. Thus it is ideal for the detection of multiple mutations at the same point (base position) or at different points of the gene or even in different genes. This method has been applied for prenatal diagnosis of genetic diseases such as thalassaemia, haemophilia and other point mutations, including short insertion or deletions (Tam J. W. O. and Woo Y. K., 1994 and references therein). Thus the method provides an economical way to introduce to the rapidly advancing nucleic acid diagnostic market. However, as in the cases of Southern, dot or slot blotting, it is still a time and reagent consuming process. Due to the exponential growth of research activity and diagnostic development, demand for a even better hybridisation procedure is imperative. The present invention describes the principle of a unique hybridisation process and a device for the said purpose whereby the hybridisation time as well as the amount of reagents used for hybridisation can be reduced by many folds.

The principle of the present invention is using the direct flow-through mechanism by which the target Nucleic acid molecules pass through the membrane pore (the membrane porosity is about 0.45 micron with about 160 micron in thinness; As it will be well appreciated by a person of ordinary skill in the art that other sizes of pores and other thickness may be used in this invention.) allowing the single strand DNA of coming in close contact with the corresponding capture complementary DNA or RNA sequences immobilized inside the membrane pores so that the target sequence can be effectively detected in high sensitivity and specificity. At present when the conventional or the reversed Dot-blot was incubated either in a glass hybridisation tubes or plastic bags in water bath or hybridisation oven maintained at appropriate temperature, the time for complete hybridisation process requires several hours to several days. The reasons for the low rate of annealing process are: 1) The need for large volume to cover the whole of the membrane is necessary. Consequently the concentration of the probe in solution available for binding the target DNA is low. Since the annealing kinetic is a bimolecular collision process, such a dilution will have enormous effect on the rate for the probe to find its target complement on the membrane; 2) During the incubation process, the majority of the solution does not make contact with the membrane. This will increase the chance of the self-annealing process of the otherwise separated complementary strands (since most of the probe or test DNA are double-stranded in origin which were denatured by heating to become single strands) DNA probe. Consequently the effective concentration of the probe is reduced further. The longer hybridisation time the lower the concentration of hybridisable single strand DNA will become resulting in still lower rate of hybridisation kinetic; and 3) In the immersion hybridisation process the most accessible target DNA molecules for probe binding are those immobilized on the surface of the membrane. Unfortunately only a small part of target DNA is actually directly facing the outside because of the intrinsic characteristics of the membrane being porous (generally from 0.1 to 0.45 micron in diameter) and therefore during the immobilized process a large part of the DNA will be immobilized in the interior part of the membrane (that is why in the blotting process smaller fragments, <500 bp for 0.45 micron and <100 bp for 0.1 micron membranes, diffuse through the membrane and lost). The rate of annealing of these target DNA will then be slowed down further by the slow diffusion process of the probe into the inside pores of the membrane. The result would be a decrease in sensitivity even with prolong incubation. A flow through hybridisation process described in the present invention eliminates all of the above intrinsic defects.

Recently a flow through hybridisation assay for oligonucleotide sequences described by the European Patent application (application number: 93,120,394.7; Publication number:605828 A1) by Felndt, H. H., Mallonee R. L. and McFarland E. C of Becton, Dickinson & Co used the immunological assay flow-through methods described in earlier arts (U.S. Pat. No. 4,366,241; 4,727,019; 4,632,901 and 4,818,677) for the detection of DNA sequences. However, this method did not have the controlled stringency elements and therefore can only be used to discriminate non-homologous sequences (even with this, there appear to produce high background noise as stated in Example 3 of document EP0 605 828 A1, page 7 line 15). It cannot achieve the required specificity and sensitivity for stringent detection even grossly related sequences. The most crucial requirement for nucleic acid hybridisation in achieving high specificity without scarifying sensitivity is the accurate control of stringency. This requirement is a must especially when discrimination amongst closely related sequences where homology is very high e.g. allelic variants, family of genes within the same organism and similar sequences from different organisms. Examples of diagnosis of genetic diseases such as the non-deletion types of thalassaemia of human beta globin genes or infectious agents like variants of HCV, HIV and others. Even in the cases of differentiating between family of genes of similar function in different organisms the flow-through process described by the prior art of Felndt et al. cannot produce the satisfactory results (see Example V of this document in later section below). The present invention discloses the methods and the apparatus necessary to achieve the most important controlled conditions for rapid and specific nucleic acid hybridisation that has never been addressed before in prior arts. The novelty of the present invention is that it can provide the controlled conditions critical for the hybridisation process which can be universally applied to all cases that is applicable to conventional Southern, Northern, Dot-Blot, Slot-Blot and Reversed-Dot Blot hybridisation techniques so far reported on the literature. When it is used for Western Blotting (protein blotting or immunoblotting), improvement on sensitivity and specificity will be expected because the reaction conditions can be accurately controlled.

SUMMARY OF THE INVENTION

This invention provides a method for determining whether a target nucleic acid sequence is present in a sample comprising steps of: (a) immobilizing probe capable of hybridizing to the target nucleic acid sequence on a matrix; (b) passing the sample through the said matrix in a flow-through device permitting formation of a complex of the target nucleic acid sequence and the probe; and (c) detecting the complexes formed, wherein a positive detection indicates the sample containing the target sequence.

This invention also provides a method for determining the amount of a target nucleic acid sequence present in a sample comprising steps of: (a) immobilizing probe capable of hybridizing to the target nucleic acid sequence on a matrix; (b) passing the sample through the said matrix in a flow-through device permitting formation of a complex of the target nucleic acid sequence and the probe; and (c) measuring the amount of the complexes formed, thereby determining the amount of the nucleic acid sequence present in the sample.

This invention provides a method for determining whether a target nucleic acid sequence is present in a sample comprising steps of: (a) immobilizing the sample on a matrix; (b) passing the probe capable of hybridizing to the target nucleic acid sequence through the said matrix in a flow-through device permitting formation of a complex of the target nucleic acid sequence and the probe; and (c) detecting the complexes formed, wherein a positive detection indicates the sample containing the target sequence.

This invention provides a method for determining the amount of a target nucleic acid sequence present in a sample comprising steps of: (a) immobilizing the sample on a matrix; (b) passing the probe capable of hybridizing to the target nucleic acid sequence through the said matrix in a flow-through device permitting formation of a complex of the target nucleic acid sequence and the probe; and (c) measuring the complexes formed, thereby determining the amount of the target sequence present in the sample.

This invention also provides the above described methods, wherein step (b) is finished in one to five minutes. In a further embodiment, step (b) is finished in one minute.

In another embodiment of the above methods, several target sequences are detected in one sample. In a separate embodiment, the target sequences are point mutations of a known sequence.

DETAILED DESCRIPTION OF THE DRAWINGS

DETAILED DESCRIPTION OF THE INVENTION

This invention provides a method for determining whether a target nucleic acid sequence is present in a sample comprising steps of:(a) immobilizing probe capable of hybridizing to the target nucleic acid sequence on a matrix; (b) passing the sample through the said matrix in a flow-through device permitting formation of a complex of the target nucleic acid sequence and the probe; and (c) detecting the complexes formed, wherein a positive detection indicates the sample containing the target sequence.

As used herein, the nucleic acids encompass both DNA and RNA. The DNA and RNA may contain all natural or synthetic nucleotides or a combination of both. This invention will work the same on various lengths of the target nucleic acid sequences.

This invention also provides a method for determining the amount of a target nucleic acid sequence present in a sample comprising steps of: (a) immobilizing probe capable of hybridizing to the target nucleic acid sequence on a matrix; (b) passing the sample through the said matrix in a flow-through device permitting formation of a complex of the target nucleic acid sequence and the probe; and (c) measuring the amount of the complexes formed, thereby determining the amount of the nucleic acid sequence present in the sample.

In an embodiment, the probe is labelled with a detectable marker. In a further embodiment, the detectable marker is selected from a group consisting of biotin, digoxigenin and colloidal gold.

This invention provides a method for determining whether a target nucleic acid sequence is present in a sample comprising steps of: (a) immobilizing the sample on a matrix; (b) passing the probe capable of hybridizing to the target nucleic acid sequence through the said matrix in a flow-through device permitting formation of a complex of the target nucleic acid sequence and the probe; and (c) detecting the complexes formed, wherein a positive detection indicates the sample containing the target sequence.

This invention provides a method for determining the amount of a target nucleic acid sequence present in a sample comprising steps of: (a) immobilizing the sample on a matrix; (b) passing the probe capable of hybridizing to the target nucleic acid sequence through the said matrix in a flow-through device permitting formation of a complex of the target nucleic acid sequence and the probe; and (c) measuring the complexes formed, thereby determining the amount of the target sequence present in the sample.

In an embodiment, the target nucleic acid sequence is labelled with a detectable marker. In a further embodiment, the detectable marker is selected from a group consisting of biotin, digoxigenin and colloidal gold.

This invention also provides the above described methods, wherein step (b) is finished in one to five minutes. In a further embodiment, step (b) is finished in one minute.

In another embodiment of the above methods, several target sequences are detected in one sample. In a separate embodiment, the target sequences are point mutations of a known sequence.

Figure 1:
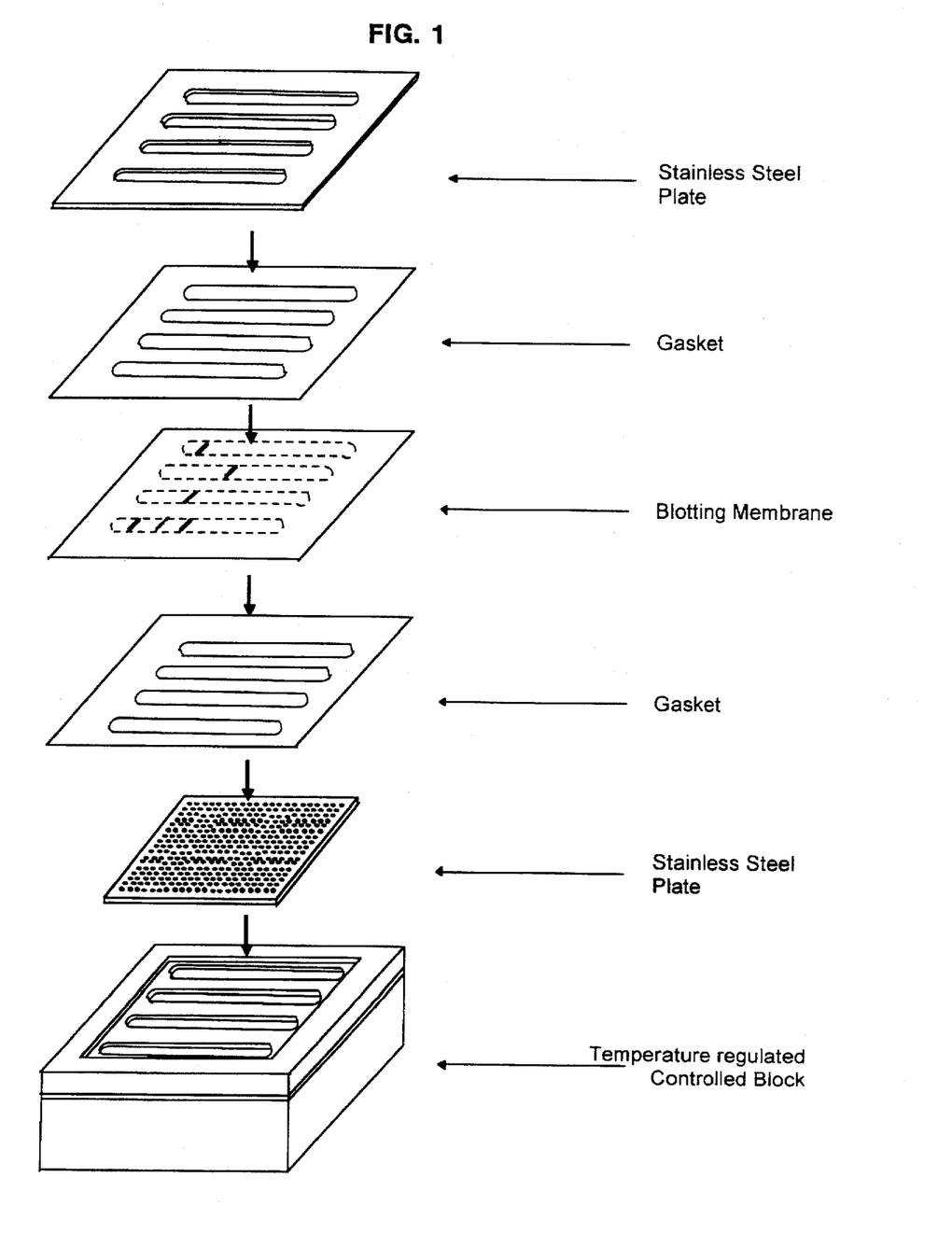
FIG. 1. is an illustration of one design of the controlled flow-through hybridisation assay device of the present invention.
Figure 2:
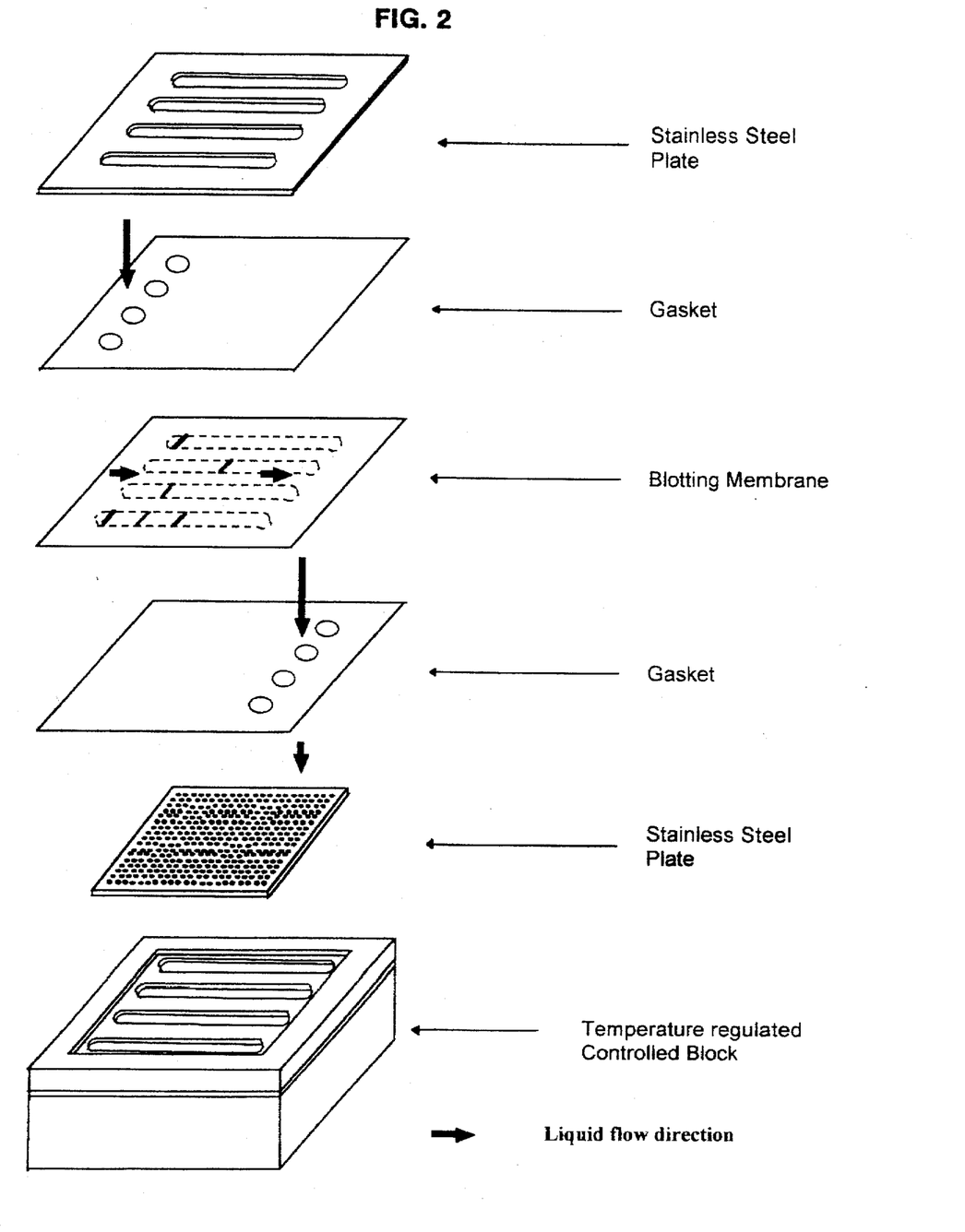
FIG. 2. is an illustration of the another process using the similar device. The change in the design of the gaskets can effectively redirect the flow of the sample to achieve a more sensitive measurement. With this embodiment plus an internal control, semiquantitative results can also be obtained. Other more sophisticated embodiments of such device can easily be constructed and modified to achieve automation and quantitative measurements.

This invention further provides the above-described methods, wherein the flow-through device is substantially the same as described in FIG. 1. In a further embodiment, the device is adjustable to the accuracy of 1 degree Celsius.

Figure 4:
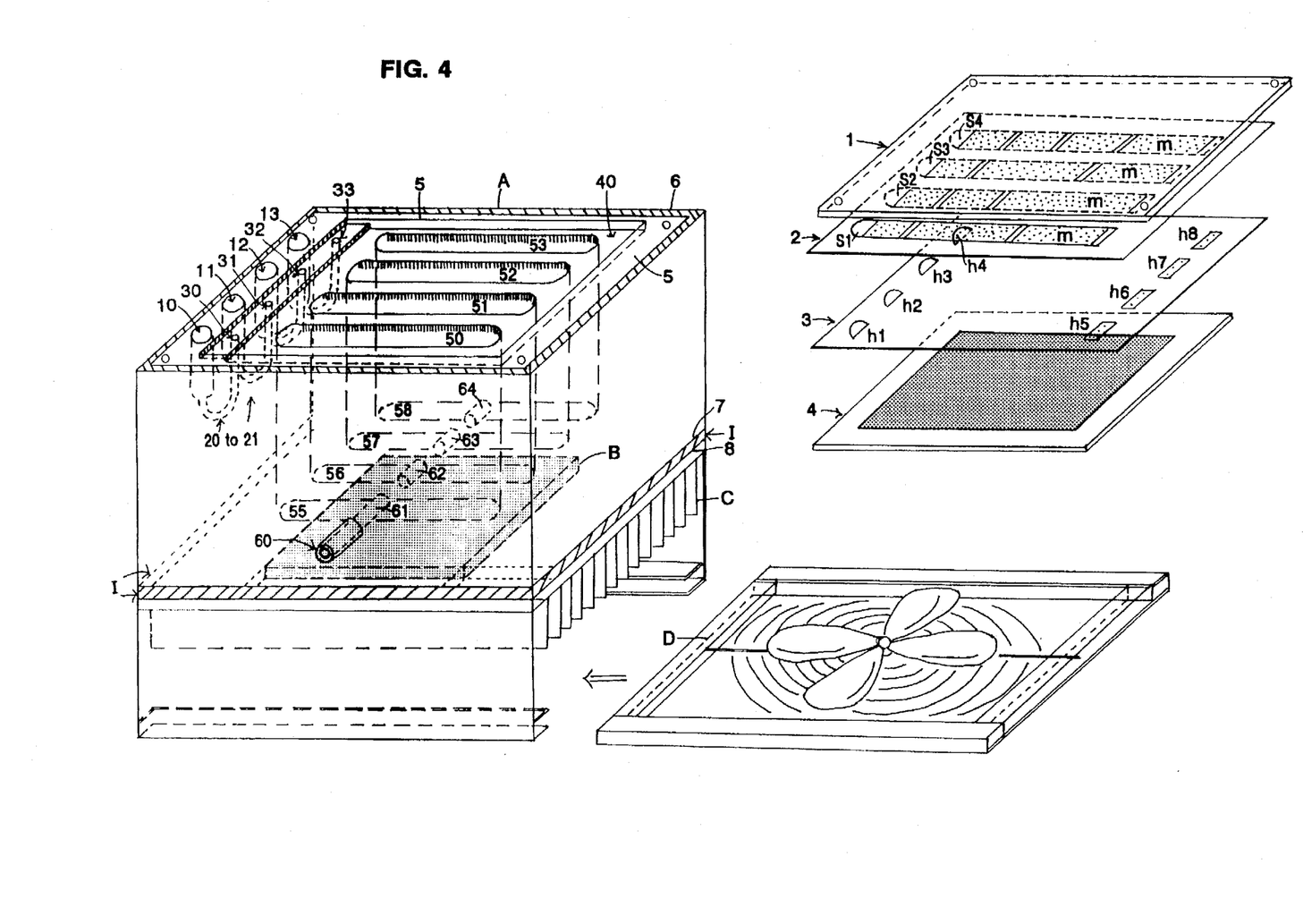
FIG. 4. Another flow-through device.
Figure 5:
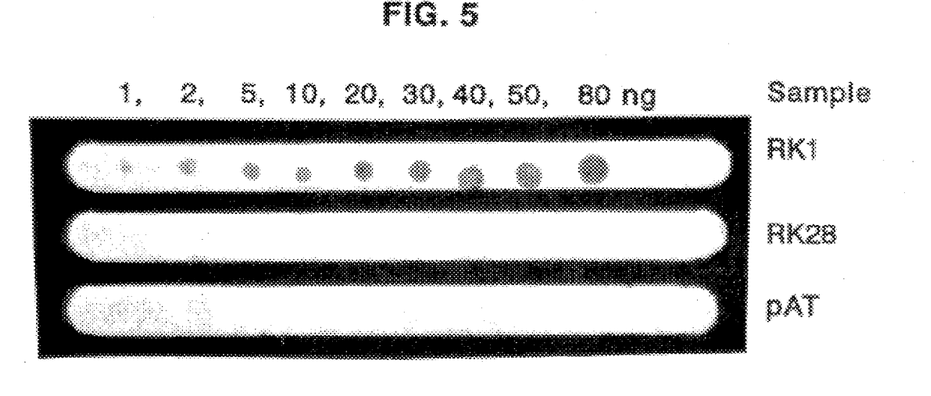
FIG. 5. The sensitivity of the flow-through hybridisation process. The hybridisation was carried out at 68° C., 3× SSC, 0.1% SDS and 10× Denharts' solution by flow-through process as described in text.

Finally, this invention provides the above-described methods, wherein the device is substantially the same as described in FIG. 4.

According to the invention, there are three essential part of the device: 1) the controlled temperature block capable of maintaining at ±0.5° C. at variable temperatures from room temperature to 70° C., the heating and regulating devices can be made of different materials. The least expensive way to maintain constant temperature of the block is by circulating heating fluid by external heating bath. Another is by incorporating the heating and cooling element directly onto the device. The applicant used the Peltier heating and cooling element for this purpose because of its simplicity. The applicant has successfully tested both prototype models. These are the simplest models. However, one may add on more sophisticated devices such as vacuum control for flow rate regulation and automatic delivery systems etc.; 2) the membrane for immobilizing the nucleic acid capture molecules which can be the DNA probe, the target DNA or oligonucleotide sequences. The immobilisation may also be in the form sandwich format: e.g. the membrane can first be coated with an affinity conjugate such as avidin to form the activated membrane. This activated membrane can be used for all tests. The specific test strip is made by adding the end biotinated DNA probe(s) of the required specific sequences onto the activated membrane for capturing the target nucleic acid molecules. The membrane can be any type such as the nitrocellulose, nylon, Nytran or the Biodynes as long as it is capable of immobilizing DNA sequences or protein conjugates in the case of sandwich assays. The applicant used the Biodyne C membrane for oligonucleotide immobilization because it gave lower background and required less blocking. In this procedure the oligonucleotide probes were covalently linked to the —COOH groups on the Biodyne C membrane via the 5'-end terminal $H_2N$-group of the modified oligonucleotides via EDC (1-Ethyl-3-(3-dimethylaminopropyl)-carbodiimide); 3) the control of the flow rate as well as the direction can be regulated by the difference in design of the gasket, the absorbent, and/or suction mechanism of the apparatus, the control block. The immobilisation of probe(s) onto the membrane can be done separately for bulk production or directly perform onto the already assembled device as shown in FIG. 1.

The present method can perform the following type of tests: 1) Southern blotting, including ZOO BLOT, analysis of genomic DNA: 5–10 ug of DNA after restriction digestion, sized by gel electrophoresis is transferred and fixed onto the membrane matrix (NC, nylon or Biodyne etc.) according to established procedures. The membrane is then placed into the flow-through device with temperature set as required, usually at 68° C. in 3× SSC and 42° C. in formamide buffers. It is understood to skilled workers in the art that other buffer component can be used. The sample(s) to be tested with appropriately labelled nucleotides is then allowed to flow through the membrane for annealing and subsequently developed into colour, chemiluminescence or autoradiograph. Similar procedures can be carried out for Northern analyses by immobilizing the RNA onto the membrane or other alternative procedures. 2) If sizing and other information are not essential, the presence of the specific sequences to be detected can be effectively done by immobilizing the specific probe or probes (separately in dots or slots, in the case of detecting multiple sequences simultaneously) onto the membrane to capture the target molecules. In general, PCR is used for amplifying the target sequences with labelled nucleotide substrate followed by flow-through hybridisation and development. 3) Reversed Blot analyses: a) Detection of point mutations, or short deletion and addition sequences: In these cases oligonucleotides are designed around the test sequences and used as probes for immobilization onto the membrane. The design of oligos should fall within a very narrow range of Tm values for all that are to be used within the same test. This is absolutely crucial for the discrimination of cross hybridisation between the mutant(s) and the normal sequences in order to eliminate false positive as well as false negative results. In this case the accurate control of block temperature is absolutely essential because the differences in Tm values of these variant sequences may be within ±2° C. Hence if there is no accurate control in hybridisation conditions, it is not possible to make the discrimination. This is the most serious defect, among other things, that the prior art described by Felndt et al.(EPO 605828 A1) can never achieve. On the contrary, the present invention provides the only solution to the problem. The capability of detecting and differentiating multiple but closely homologous sequences simultaneously by flow-through method is novel only to this invention. B) Detection of unrelated sequences simultaneously by flow-through method: Unique sequences of specific gene(s) from the same organism (e.g. different regions of the same gene or different genes all together) or from different organisms (e.g. pathogens such as viruses, bacteria, parasites and others) are designed and synthesized, preferably having close range of Tm values for covalent binding to the membrane as probes for capturing the target nucleic acid sequences. Again the target sequences for the flow-through hybridisation can be generated by PCR or any other amplification process with the incorporation of labelled nucleotide enabling the generation of sensitive signals as described elsewhere and this invention. The target sequences can be labelled or amplified by PCR, SDA or any other incorporation method. The available methods such as the radioactive nucleotides, the digoxigenin, the biotin and the S-nucleotide are equally suitable. The signal can be followed by autoradiography and nonradioactive labelling technologies of enzyme-linked-immobilized assays (ELISA). Applicant has satisfactory results for both the colour development of AP and HRP and the chemiluminescence emission processes (ECL).

It has been reported that for quantization, the branch DNA test advanced by Chiron (Hendricks-DA, et al., 1995 and references therein) is more reliable because the signal amplification is directly proportional to the endogenous concentration of the target sequences before amplification with methods such as the PCR, (Mullis and Faloona, 1987) SDA (Laffler-TG et al., 1993) or LCR (Walker G. T., 1993), a step that may not be quantitative. The present flow-through method can be applied equally well to this test because it too must go through the hybridisation process.

The Flow-through Hybridisation Device

Figure 3:
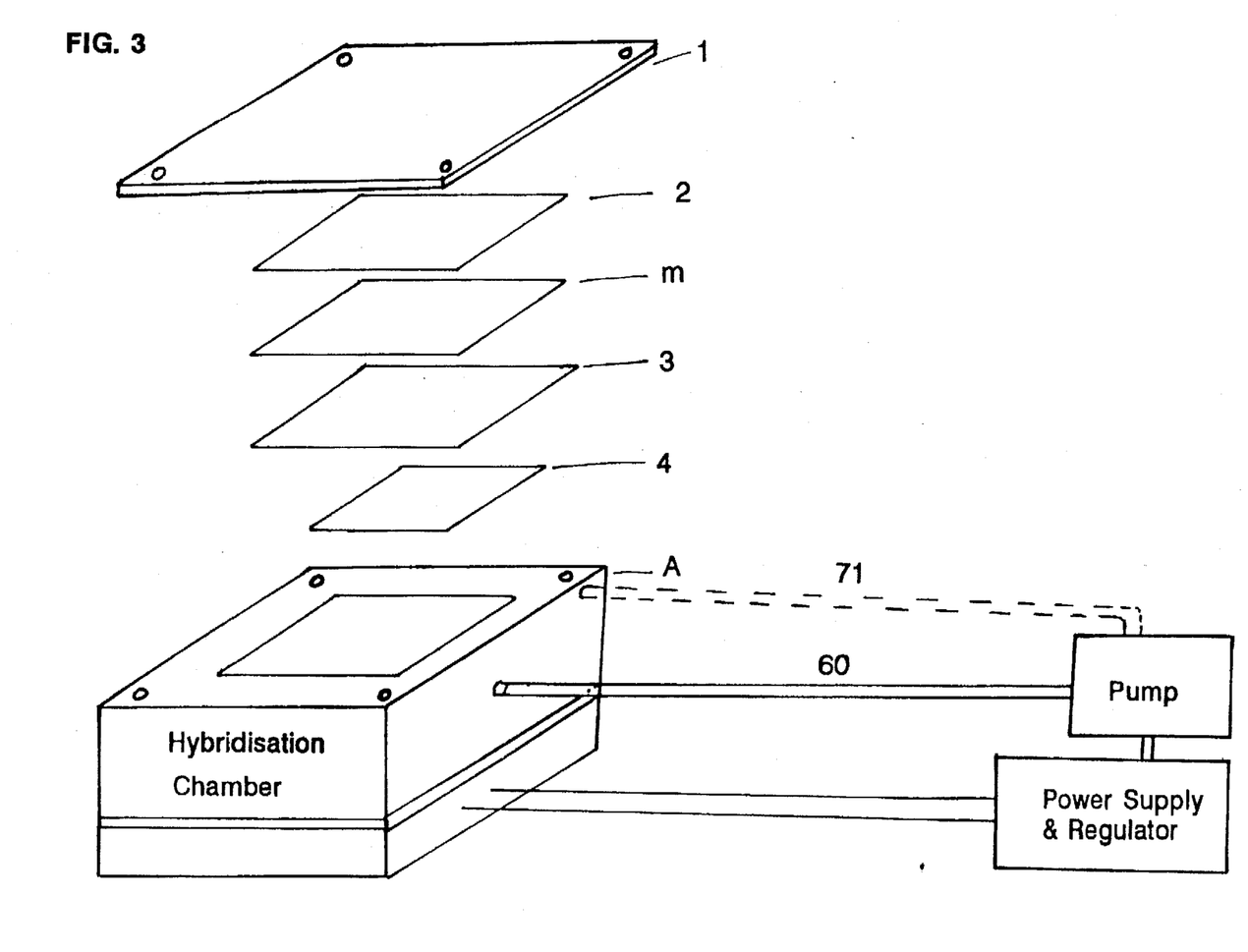
FIG. 3. A flow-through device system.

The complete embodiment includes three essential elements as shown in FIG. 3: the temperature regulated flow-through hybridisation chamber; the peristaltic pump; and the DC power supply. The pump and the power supply are readily available commercially. However the heart of the unit is the specially designed temperature regulated Chamber. The arrangement of the complete unit is given in FIG. 4. It is understood that this is just a simple arrangement. Others can be employed within the general concept of the present invention. To those skilled in the art of electomechanic designer, one of the obvious embodiment is to put the power supply and pump attached to the hybridisation chamber to form a single self-sustained unit.

The detail preferred design of the present embodiment is given in FIG. 3 and 4. The main chamber unit is composed of two main parts: the hybridisation chamber (designated as 'A') and the heating-cooling unit (designed as B, C, and D). "B" is an Peltier electronic heating cooling module; "C" is the metal heat exchange unit and "D" is the cooling fan.

The main hybridisation chamber A consists of the metal block 5 covered by the outer insulation 6 which is made of polyurethane to prevent heat exchange to the surrounding so that the temperature of the block 5 can be kept constant uniformly through out the block. The heating or cooling is supplied by the electronic heating/cooling unit B, the Peltier module, which is powered by the power supply and regulator unit PSR. The upper surface of the Peltier module B is attached to the bottom, 7, of block 5 and the other side is attached to 8, the top surface of the heat exchanger C. The insulator layer I is to prevent heat transfer from the bottom of block 5 to the heat exchanger C through 7 to 8 and vice versa. To increase the efficiency of heat exchange the cooling fan D is placed directly under the unit B.

In FIG. 4, the metal block is preferably good heat conductor metal, like alumina, copper, stainless steel and other materials. Alumina is generally preferred because of its high efficiency for heat transfer. However, during the hybridisation process, various solutions will come in direct contact with the metal, an inert coating is preferred to prevent unnecessary chemical reaction between the solution and the metal surface. This may be anodisation, Teflon coating or other inert painting by various process already disclosed or new process of future arts. It is understood that the better heat transfer material the more efficient for accurate temperature control through out the test surface of the membrane. For simplicity however, the present device used for the pilot tests, the chamber A was made of stainless steel. This is because stainless steel is inert to the solutions applicant used. However because its heat transfer efficiency is much lower than allumina, the temperature across the test surface (e.g. the membrane strips (m) shown in 2 of FIG. 4), particularly along the edge, may be less uniform. In addition, it may take longer to achieve the temperature equilibrium. Nevertheless, although it took a little longer time initially to equilibrate the block temperature before carrying out the flow-through hybridisation processes, the results were very satisfactory. The top most cover of the present embodiment, 1, is made of the same heat conducting metal. Other materials such as clear plastics can also be used. The gaskets 2 and 3 are made of heat conducting material such as GAP-PAD™ from The Bergquist Co. The metal plate 4, having small holes to allow liquid to pass through, is directly placed on the inner surface 40 of the main block 5 in chamber A. Hence in this embodiment, 1 to 5 are assembled together by screws S to become a single unit. It is understood that other methods known to skilled workers of the arts can be used. Referring to the hybridisation chamber A, the hollow slots 50 to 53 provide the draining routes for the solution to flow-through the membrane via the connecting drainage 61 to 64 and 60. The flow rate, if needed, is controlled by the peristaltic pump P connected to 60. For simple flow-through process, the slots 50 to 53 can be filled with absorbent paper allowing the solution to come in contact. The liquid flow could be carried out by capillary action. This is particularly relevant if solution and sample are delivered by droppers. The bottom of each slots designed 55 to 58. It is understood that these slots can be replaced with other forms (e.g. it can be a hollow rectangular space filled with absorbent paper and an outlet similar to 60 and 61. If vacuum or controlled of the flow rate is needed, connect 60 to the pump P). Re-circulation can also be done through the return path 71 for continuous incubation, if needed. Although this is not necessary for the purpose of the present flow through process because very little volume of prehybridisation solution, sample or washing liquid is required and that the hybridisation is very efficient. However in cases when extremely dilute samples of large volume is to be tested such embodiment might be beneficial. The reservoirs 10 to 13, made as part of the metal block 5, are filled with incoming solution, sample and washing solution etc. The liquids are equilibrated to the required temperature and consequently pass through the opening paths 20 to 23 and finally flow through the membranes through the openings 30 to 33. The embodiment shown in 1 to 3 is designed for semiquantitaive measurements. Other arrangements can be modified by changing the design of the gaskets. The strips shown here is the preferred setting. The number of slots can be variable. It can be set like the ELISA format e.g. an arrays of circular holes. Each hole can have many dots for multiple analytes plus controls analysis. It can also be a sheet of membrane filter similar to the normal Southern Blotting hybridisation.

Other than the embodiment shown in FIG. 1 and examples given in this document, the present device in use is described in detail: The membrane strips were inoculated with the capture nucleic acid probes, placed onto the slots of the gasket 2 and assembled as described above from 1 to 5. The reservoirs 10 to 13 are filled with pre-hybridisation solution such as SSC (as described in the Examples or others) and drawn to flow-through the membrane strips in the direction from 10=>20=>30=>h1=>S1 rightwards along the membrane strips m. The liquid continue to flow through h5=>51 and downwards to the absorbents. The controlled rate of flow will be achieved through the pump P via drainage path 60. Next the testing samples are filled the same way and then the washing solutions. After washing the temperature of Block 5 is lowered to the required setting for colour development. Again by similar flow through process. The exact procedures are dependent upon the developing system used as described in Examples below. In this particular process, all the solution or samples will pass through the membrane strip to come into contact with the probes. For this reason, quantitative results are expected as long as the solution flow rate is adjusted to allow adequate time for binding equilibrium. Since it was shown that the time required to achieve maximum sensitivity (see Example II Table I). It is understood that other arrangement will work within the scope of this flow-through concept. In the downward flow-through tests given in Examples in this document, a large amount of liquid was actually wasted because it flowed-through parts of the membrane that did not have capture molecules. However, the gasket below the membrane can be modified where the openings are directly below the test dots. Thus the solution will be redirected towards the capture molecules. Such arrangements will increase the detection to a much lower limit. Although such data is still unavailable, based on mathematical concept, the result is entirely reasonable.

The embodiment given here in FIG. 4 is only a representative example. Other more sophisticated module easily designed by skilled workers in the art based on the general concept of the present invention. The use can cover all kinds of hybridisation processes of nucleic acid. When adopted to immunoassays, this controlled device should provide much improvement.

The invention will be better understood by reference to the Examples which follow, but those skilled in the art will readily appreciate that the specific experiments detailed are only illustrative, and are not meant to limit the invention as described herein, which is defined by the claims which follow thereafter.

EXAMPLE I

Test for the Sensitivity and Specificity

This experiment was designed to test the efficiency of the apparatus based on the flow-through principle. Experiment was carried out on the prototype of the flow through device. Heat denatured (or alkaline denatured) DNA of specific sequence (e.g. in this example Human globin gene sequence the PstI 4.4 kb fragment was used) of various concentrations were immobilised onto the Nitrocellulose membrane (or any other membrane used for Southern blotting analysis). In parallel, similar quantities of control DNAs, RK28 and pAT, were added in different lanes to test if there is any cross hybridisation between these different sequences. The test DNA sample was generated by PCR as follows: lug of genomic human DNA was used as template and the polymerisation carried out in the presence of 1 unit of Taq polymerase (AMPLITAQ by Perkin Elmer Cetus), biotin-11-dUTP and dNTPs according the protocol provided in the PCR kit (Prekin-Elmer Cetus Corp). The DNA was first denatured at 94° C. for 4 minutes followed by cycling program: DNA denaturation at 94° C. 1 minute, annealing at 54° C. 1 minute and 72° C. 1 minute extension ime for 30 cycles with final extension of 10 minutes. The two primers, 5'-d(TCATTCGTCTGTTTCCCATTCTAAA)-3'(SEQ ID NO.: 1) and 5'-d(GGACAGGTACGGCTGTCATCACT-bx;1TA)-3'(SEQ ID NO.:2), used were within the human beta-globin sequence franking the exons I and II producing a 760 bp fragment. The purity was checked by agar gel electrophoresis. The hybridisation device, the metal block, was maintained at 68° C. and all other hybridisation solutions were kept at the same temperature. The following protocol was used in the flow-through process: 1) Prehybridisation was done by incubating 0.5 ml of blocking solution A (Solution A: 3× SSC, 0.1% SDS, 10× Denhardt's solution and 100 ug/ml of denatured salmon sperm DNA. It is understood that other blocking or hybridisation solutions can be used as well. It is also understood that the hybridisation conditions may vary depending on the components in the blocking solution, the DNA sequence and the temperature setting. For example this same reaction when carried out with the Boehringer Mannheim's Digoxigenin (DIG) labeled DNA kit the temperature was set at 65° C. in 5× SSC, 0.1% N-lauroylsarcosine, 0.02% SDS and 1% Blocking solution, BM#1093657.). 2) 10 ul of the PCR product mixed with 40 ul solution A, was heat denatured at 95° C. on the heating block. Mixed with 0.5 ml of solution A, 68° C., then dropped onto the membrane. 3) Washed twice with 0.5 ml of solution A. 4) Lower the temperature of the block to room temperature (37° C. worked equally well) followed by dropping 0.5 ml of the Streptavidin-HRP conjugate. 5) Washed with another 0.5 ml of the reaction solution B (0.1× SSC and 0.1% SDS. It is understood also that solutions of other components can be used). 6) Colour development can be done on the device or the membrane be taken out into a plastic box for processing. The time required, from step 1 through step 5, was about 3–5 minutes. Step 6 required 30 minutes which is similar for other procedures. However if chemiluminescence is used, the process takes about 2 minutes; colloidal gold conjugate detection for less than 1 minute. FIG. 4 shows the results of these experiments. It was clear that there was no cross hybridisation between the beta-globin sequence probe with the DNA controls e.g. no hybridisation signal obtained for RK28 and pAT. The lowest concentration used was 1 ng ($3.25 \times 10^{-16}$ mole) when the Avidin-HRP colour development system was used. 50 pg ($1.6 \times 10^{-17}$ mole) can be detected by chemiluminescence. The sensitivity and specificity were found to be equal or better than the parallel experiments using the conventional Southern hybridisation procedures. However, the hybridisation time required for the flow-through process was less than one minute whereas over 6–10 hours was used for conventional hybridisation techniques. Another important consideration was the fact that using the present procedures a 20–100 folds reduction of the sample and reagents were achieved. This alone would provide enormous saving of resource and time making it much more efficient and affordable.

EXAMPLE II

The Rate of Hybridisation in the Flow-Through Process

In order to determine the optimal condition of the flow-through hybridisation process, the applicant has performed a series of experiments to determine the effective sensitivity of detection against flow rates. The protocol used was similar to that used in Example I above. 10 ng ($3.3 \times 10^{-15}$ mole) of the human beta-globin DNA was immobilized onto the membrane for each determination. Again 1ug of human total DNA was amplified for 30 cycles to produce the biotinated globin DNA fragment. 10 ul of this stock was diluted to 0.5 ml, denatured by heating and than flowed through the membrane for annealing at identical condition as above except the flow-through time was controlled at specified time. The conventional hybridisations were carried out with the same kind of membrane and DNA quantity which was placed into a plastic bag, prehybridized in solution A at 68° C. in water bath for 6 hours. In order to cover the whole membrane the total volume used for the hybridisation was 5 ml. 10 ul of the denatured biotinated DNA was then added into the bag for hybridisation at 68° C. After specified time the membrane was washed and colour development carried out as described. The intensity was determined using the BioRad imaging master. The results are given in Table I. It is clear that one minute flow rate was sufficient to achieve over 80% of the sensitivity. On the other hand, the conventional hybridisation method gave less than 20% sensitivity after 30 to 60 minutes hybridisation. Hence this flow-through process is far superior to the conventional method, both in time and consumable savings.

TABLE I

Relative Rate of Hybridisation

| Time (min) | % Intensity | |
|---|---|---|
| | Flow-through | Conventional |
| 1 | 180.2 | not done |
| 3 | 89.1 | not done |
| 5 | 95.5 | not done |
| 30 | not done | 35.6 |
| 360 | not done | 100* |

*6 hours to overnight hybridisation used as reference

EXAMPLE III

Simultaneous Detection of Multiple Samples as Well as Multiple Sequences of Different Origin DNA of four different sequences were dotted onto the NC membrane at 5 ng concentration as described in Example I in the same slot. Four identical slots were immobilized with the same set of DNA samples to capture the labeled DNA probes. These four DNA were: a) the 4.4 kb PstI (RK1) genomic fragment of human beta-globin gene. This fragment contains the whole globin gene which includes all three exons (I, II and III) and the introns; b) the exon III (E3) sequence of the globin gene; c) the 867 bp of the human insulin receptor(hIR) cDNA consisting the exons 10–12; and d) the mouse thymidylate synthase (TS) cDNA. Two DNAs were used as negative controls to test for background hybridisation. They were the plasmid vector DNA (pAT) and a plasmid sequence containing the human alfa-globin cDNA fragment (JW101). The following PCR DNA fragments were generated with biotin-labelled dUTP as described in Example I used as probes: #1) Exons I and II human globin sequence; #2) Exon III of human globin; #3) 280 bp of the mouse TS cDNA sequence and #4) the 216 bp IR cDNA sequence. The expected positive hybridisation results will be as follows: 1) Probe #1 (Exons I and II) can only hybridize with RK1; 2) Probe #2 (Exon III) will hybridize with both RK1 and E3; 3) Probe #3 (hIR) can only hybridize with hIR; whereas 4) Probe #4 (the TS sequence) can only hybridize with TS sequence. In this example similar procedures and hybridisation conditions as stated in Example I were used. Lane 1 was hybridized with PCR probe #1; lane 2 with a mixture of probes #2&3; lane 3 with #4 ; and lane 4 with probes #2,3 &4. The results are given in Table II. As expected in column #1 (lane 1) only RK1 gave positive signal; in column #2(lane 2) RK1, E3 & hIR were positive; in column #3(lane 3) only TS showed positive signal; and in column #4(lane 4) all except the negative control samples (pAT and JW101) gave clear positive results. The data clearly show that if stringent conditions could be maintained, there would be no cross hybridisation reaction with either single or even a mixture of multiple DNA sequences.

TABLE II

| | probe (fragment) used | | | |
|---|---|---|---|---|
| Sample | #1 | #2 & 3 | #4 | #2, 3 & 4 |
| pAT | − | − | − | − |
| JW101 | − | − | − | − |
| RK1 | + | + | − | + |
| E3 | − | + | − | + |
| hIR | − | + | − | + |
| TS | − | − | + | + |

EXAMPLE IV

Simultaneous Detection of Multiple Point Mutations of the Same Sequence

Figure 6:
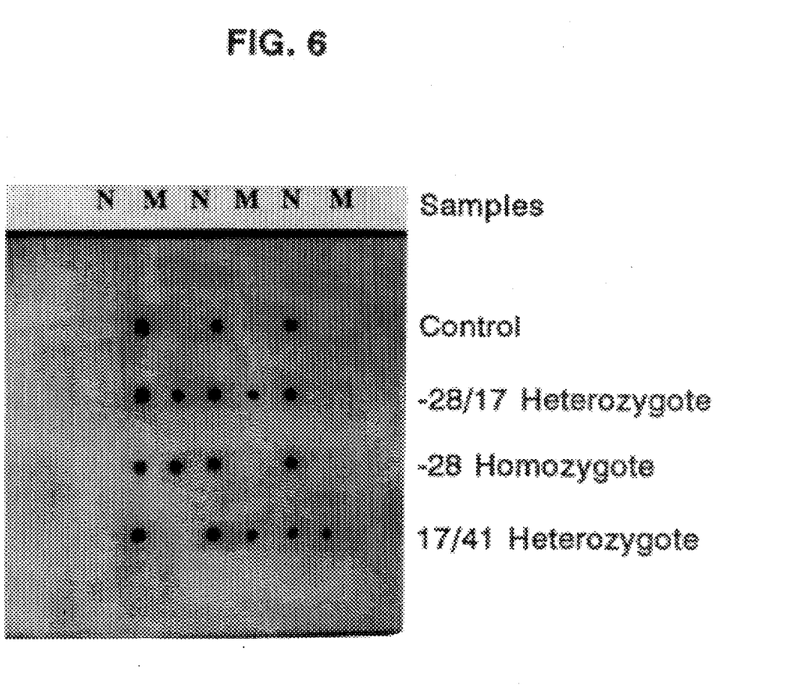
FIG. 6. Detection of single point mutations. N: normal DNA sequence; M: point mutation from the normal sequence. The numbers represent the position of the mutation within the globin gene. The hybridisation was carried out at 42° C. in 2× SSC, 0.1% SDS solution.

In this experiment single strand oligonucleotides of 17–24 bases were synthesized according to specific gene sequences of detection for the capture of corresponding complementary sequences. The Tm value of each of these oligonucleotides was carefully designed to be within 2° C. relative to all those used in the same test group. The 5'ends of each of these oligos were modified with the $H_2N-(CH_2)_3-$ moiety enabling them to be covalently linked to the membrane. Biodyne C membrane was used because the membrane contain the reactive group —COOH. The immobilization of the oligos were done according to established procedures (J. W. O. Tam 1995 & Maggio et al., 1993): The membrane was treated with 0.1N HCl, rinsed with double distilled water followed by treatment with aqueous EDC (0.8 g in 5 ml water) for 15 minutes and then blot dry with Watman filter paper. The $H_2N$-oligos were dissolved in 0.5M $NaHCO_3$/$Na_2CO_3$ to a final concentration of 10 pM. 1 ul of each oligos were dotted onto the above membrane, stand for 10–15 minutes and the membrane is then neutralized with 0.1N NaOH for 10 minutes, rinsed with water and blot dry. The test membrane can be stored in plastic bag under nitrogen for latter use. When test, the appropriate membrane is assembled into the flow-through hybridisation device as shown in FIG. 1. The temperature of the device and all solutions were maintained at 42° C. Wet the membrane (9×7 cm) with 0.5 ml 2× SSC, 0.1% SDS followed by 0.5 ml of the denatured PCR target DNA products generated as described above. The unbound biotinated. PCR product was washed out with 0.5 ml 2× SSC, 0.1% SDS followed by same with 0.1M sodium citrate, pH 7.0., 0.5 ml of 1:2000 dilution of the streptavidin-HRP from Boehringer Mannheim was flowed through followed by washing and proceeded to colour development with TMB as described by the manufacturer(BM). In this example, applicant used four genomic DNA samples from our pool of thalassemic patients whose DNA had already been characterized by DNA sequencing. All of them have point mutations or short deletions in their beta-globin DNA coding region. These are the most common defects among the beta thalassemia lesions in Hong Kong and Southern Chinese. The numbers refer to the base position or codon number in the coding region with the transcription initiation site being 1. −28 refers to a single base change in the DNA base position 28 upstream (5') from the initiation site (e.g. A=>G change from normal to mutant). 17 refers to a single base change in codon position 17 (e.g. A=>T at base position 102). 41 is a short deletion of 4 bases (TCTT) in codon 41. The oligonucleotides immobilized onto the membrane in each lane were as follows: column 1 is the normal sequence, GCTGGGCATAAAAGTCAG (SEQ ID NO.:3), near position −28; column 2 is the mutated sequence, GCTGGGCATAGAAGTCAG (SEQ ID NO.:4) around position −28; column 3 is the normal sequence, CTGTGGGGCAAGGTGAA (SEQ ID NO.:5), centered at codon 17; column 4 is the mutated sequence, CTGTGGGGCTAGGTGAA (SEQ ID NO.:6), around codon 17; column 5 is the normal sequence, AAGGACTCAAAGAACCTCT (SEQ ID NO.:7), near codon 41; column 6 is the abnormal sequence, CAGAGGTTGAGTCCTTTG (SEQ ID NO.:8) near codon 41. The two PCR primers used are: 5'GGACAGGTACGGCTGTCATCACTTA3' (SEQ ID NO.:2) and 5'TCATTCGTCTGTTTCCCATTCTAAA3' (SEQ ID NO.:1). The biotinated amplified products of each of the four patient DNA samples were generated the same way as described in Example I. Patient 1 was found to be heterozygote of point mutations. One chromosome carries the −28 mutation and the other chromosome at codon 17. Patient 2 was homozygotic mutations in both chromosomes at position −28. The third patient carries the point. mutation at codon 17 in one chromosome and a four bases deletion at codon 41 in the other. The normal control DNA was isolated from an individual having the normal globin DNA gene sequence. Evidently as shown in FIG. 6, the results obtained were exactly as expected. There were neither false positive nor false negative observation in these single point mutation diagnostic tests. It is worth pointing that if the conventional hybridisation method were to be used, a total of 24 experiments have to be performed. The flow-through hybridisation assay described by Becken Dickinson & Company as it stands can not discriminate any of these point mutations, because the same experiment done at room temperature resulted in ALL positive for all dots (see example VI below) because of the low stringency. Clearly again, this invention is novel and unique on its own right.

EXAMPLE V

Figure 7:
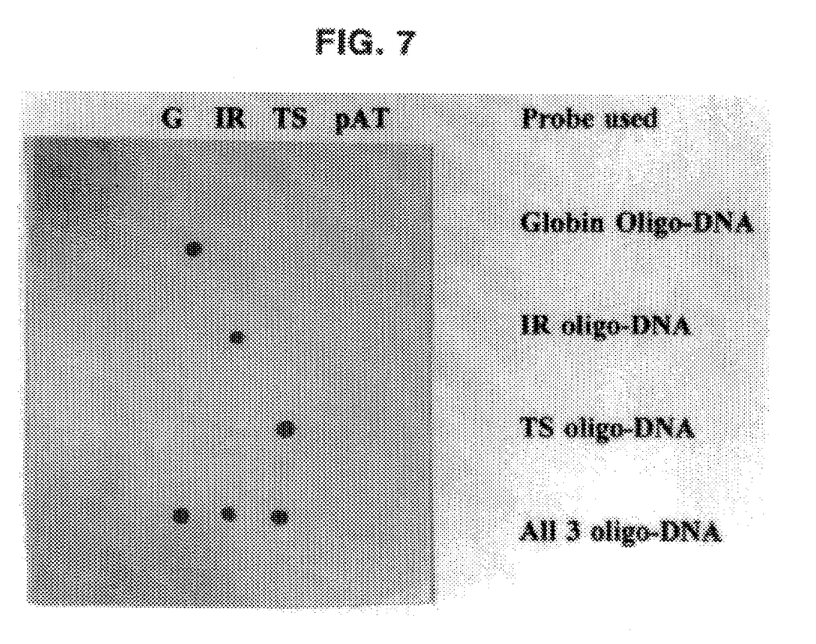
FIG. 7. Detection of different DNA sequence simultaneously. G: Human beta-globin gene IR: Mouse insulin receptor gene TS: Ascaris Suum thymidine synthetase gene PAT: Control bacterial plasmid FIG. 8. The results of detecting single point mutations at low stringency. N: normal DNA sequence; M: point mutation from the normal sequence. The numbers represent the position of the mutation within the globin gene. The hybridisation was carried out at 37° C. in 2× SSC, 0.1% SDS solution. In contrast to FIG. 6 above, no discrimination was obtained between normal and mutant sequences.

Detection of Multiple Sequences of Unrelated Origin by Oligonucleotide Probes Simultaneously The present flow-through assay can be applied to detect the presence or absence of different sequences simultaneously. In this example applicant immobilized four different oligonucleotides onto the test membrane to capture the human beta-globin (G), the rat insulin receptor (IR), the Ascaris Suum thymidylate synthetase (TS) and the plasmid pAT DNA sequences. Again the biotinated DNA of the above DNA sequences were synthesized by PCR separately. The hybridisation protocol of Example 6 was used. FIG. 7 shows the results of four separate hybridisations: lane 1 hybridized with only the globin DNA; lane 2 with IR; lane 3 with TS and lane 4 with all three biotinated DNA sequences. As expected in lane 1 the globin sequence (G) hybridized only with the globin oligo-DNA; in lane 2 the IR sequence only annealed with the IR oligo-DNA; in lane 3 the TS sequence binded specifically with the TS oligo-DNA probe whereas in lane 4 all three sequences (G, IR & TS gave positive results at the corresponding dots. In all cases the plasmid pAT did not show any cross hybridisation with any of these sequences. Thus it was clear that hybridisation was very specific e.g. each lane produced definitive hybridisation signals with neither false positive and nor false negative results. Similar experiments were applied to the diagnosis of pathogens such as HIV and hepatitis viruses, bacteria and parasites all in one panel with the use of this flow-through procedure together with the controlled hybridisation device (data not shown). The specific oligonucleotides for the capture of the HCV and HBV were synthesized with the $H_2N$- reactive group attached to the 5'-end for covalent linkage ($H_2N$-5'-dCCATGGCGTTAGTATGAGTGTCGTGCA (SEQ ID NO.:9) and $H_2N$-5'-dGATTCCTATGGGAGTGGGCCTCGTCC (SEQ ID NO.:10) respectively). Another two pairs of primers were used for PCR amplification of the two target DNA sequences in the presence of biotinated nucleotide as the label for colour developments. This example clearly demonstrated the superior potential of the present invention to carry out specific DNA hybridisation in an un-surpass speed and sensitivity.

EXAMPLE VI

Figure 8:
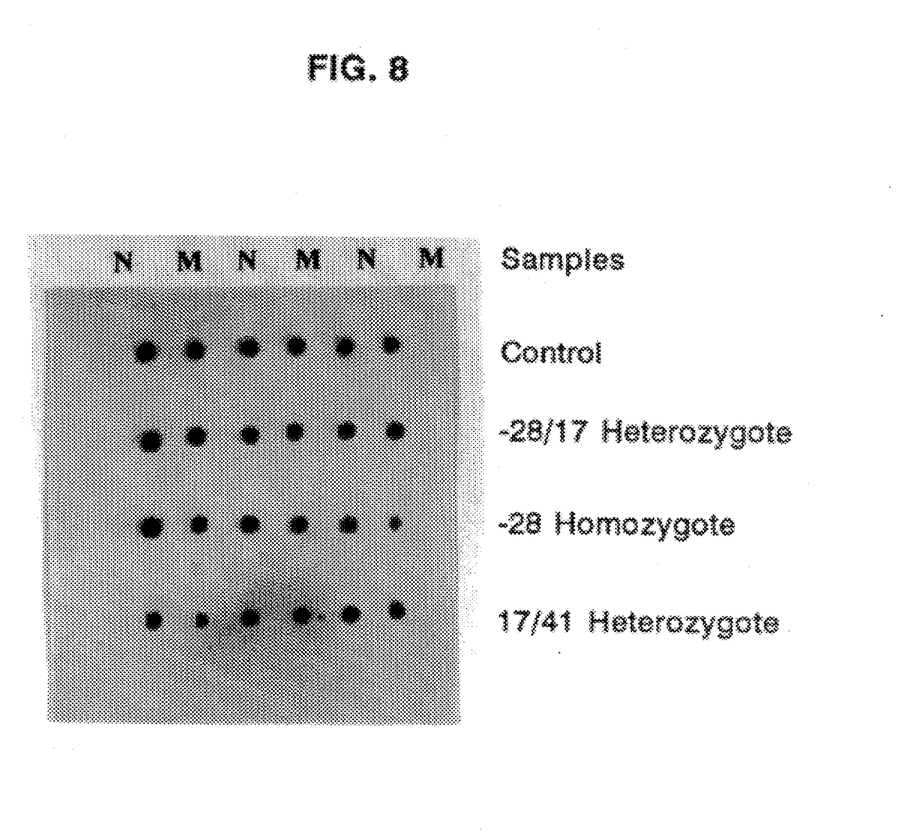

To Demonstrate the Clear Advantage of the Present Flow-Through DNA Hybridisation Process Over Similar processes of the prior arts 1) Specificity: As pointed out above that stringency is the most important requirement to achieve the specific hybridisation. This critical requirement was neither discussed in the document EPO 605828 A1 by Fednlt et al. nor was there any evidence given in this prior art on the flow-through application process. In fact all prior arts dealing with nucleic acid hybridisations to perform in specific conditions, such as the solution medium, the temperature and time. In order to clarify this point, applicant carried out identical tests given in the Example IV above, except that the temperature was kept at 37° C. instead of 42° C. FIG. 8 below shows the result of such tests. In all cases, lane 1 through lane 4, every dot gave a clear positive result indicated that there is no discrimination between the normal and mutant sequences. In fact similar results were obtained with temperature set at 40° C. and at room temperature suggesting that the flow-through format described by the document EPO 605828 A1 is not applicable for most nucleic acid, DNA and RNA, hybridisations. This was well known to those skilled in the appropriate arts. This is the reason why instrument like hybridisation ovens and hybridisation chamber were produced and being used wildely. Recently a patented temperature regulated hybridisation chamber was described (U.S. Pat. No.

5,466,603). Unfortunately such a device is still aiming for the conventional hybridisation process. The present invention is a totally new to any prior arts.

2) Versitality: The present art as described can be applied to any process that hybridisation processes e.g. Southern, Northern and Western Blottings. It can be applied to large DNA fragments as well as small oligonucleotides hybridisations. As shown in the above examples, it can be used to detect minimal variations of sequences and mulitples samples is a single strip. The most advantage for the present invention is its ability to carry out the detection in minimal time and materials.

References:

Antonarakis, S. E. et al., (1988), Brit. J. Haemat. 70, 357–361.

Britten and Kohne, (1968), Science 161, 529–540.

Hendricks, D. A., et al., Am. J. Clin. Pathol. (1995) Nov; 104: 537–46

Huang C. H., Lam V. M. S. and Tam J. W. O., (1988), in Birth Defects: Original Article Series, Vol. 23 #5A, 125–131.

Laffler, T. G. Carrino J. J. and Marshall R. L., Ann. Biol. Clin. Paris. (1993); 51: 821–6.

Maggio, A. et al., (1993), Blood, 81, 239–42.

Miller, J. R and Koopman M, (1990), Animal Genetics, 21, 77–82.

Mullis, K. B. and Faloona, F. A., Methods Enzymol. (1987), 155, 335–350.

Southern E. M. (1975), J. Mol. Biol. 98, 503–517.

Tam J. W. O. and Woo Y. K., The Proceeding of The Miami Winter Symposium on the Biotechnology and Gene Technology, (1994) in press.

Walker G. T., PCR Methods Appl. (1993); 3, 1–6.

What is claimed is:

1. A method for determining whether a target nucleic acid sequence is present in a sample comprising steps of:
   (a) immobilizing probe capable of hybridizing to the target nucleic acid sequence on a matrix;
   (b) passing the sample through the said matrix in a flow-through device permitting formation of a complex of the target nucleic acid sequence and the probe, wherein this step is finished in one to five minutes; and
   (c) detecting the complexes formed, wherein a positive detection indicates the sample containing the target sequence.

2. A method for determining the amount of a target nucleic acid sequence present in a sample comprising steps of:
   (a) immobilizing probe capable of hybridizing to the target nucleic acid sequence on a matrix;
   (b) passing the sample through the said matrix in a flow-through device permitting formation of a complex of the target nucleic acid sequence and the probe, wherein this step is finished in one to five minutes; and
   (c) measuring the amount of the complexes formed, thereby determining the amount of the nucleic acid sequence present in the sample.

3. A method according to claim 1 or 2, wherein the probe is labelled with a detectable marker.

4. A method according to claim 3, wherein the detectable marker is selected from a group consisting of biotin, digoxigenin and colloidal gold.

5. A method for determining whether a target nucleic acid sequence is present in a sample comprising steps of:
   (a) immobilizing the sample on a matrix;
   (b) passing the probe capable of hybridizing to the target nucleic acid sequence through the said matrix in a flow-through device permitting formation of a complex of the target nucleic acid sequence and the probe, wherein this step is finished in one to five minutes; and
   (c) detecting the complexes formed, wherein a positive detection indicates the sample containing the target sequence.

6. A method for determining the amount of a target nucleic acid sequence present in a sample comprising steps of:
   (a) immobilizing the sample on a matrix;
   (b) passing the probe capable of hybridizing to the target nucleic acid sequence through the said matrix in a flow-through device permitting formation of a complex of the target nucleic acid sequence and the probe, wherein this step is finished in one to five minutes; and
   (c) measuring the complexes formed, thereby determining the amount of the target sequence present in the sample.

7. A method according to claim 5 or 6, wherein the target nucleic acid sequence is labelled with a detectable marker.

8. A method according to claim 7, wherein the detectable marker is selected from a group consisting of biotin, digoxigenin and colloidal gold.

9. A method according to claim 1, 2, 5 or 6, wherein step (b) is finished in one minute.

10. A method according to claim 1, 2, 5, or 6, wherein several target sequences are detected in one sample.

11. A method according to claim 10, wherein the target sequences are point mutations of a known sequence.

12. A method according to claim 1, 2, 5 or 6, wherein the flow-through device is as described in FIG. 1.

13. A method according to claim 1, 2, 5, or 6, wherein the device is adjustable to the accuracy of 1 degree Celsius.

14. A method according to claim 13, wherein the device is as described in FIG. 4.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:1:

TCATTCGTCT GTTTCCCATT CTAAA 25

( 2 ) INFORMATION FOR SEQ ID NO:2:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:2:

GGACAGGTAC GGCTGTCATC ACTTA 25

( 2 ) INFORMATION FOR SEQ ID NO:3:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:3:

GCTGGGCATA AAAGTCAG 18

( 2 ) INFORMATION FOR SEQ ID NO:4:

( i ) SEQUENCE CHARACTERISTICS:
    ( A ) LENGTH: 18 base pairs
    ( B ) TYPE: nucleic acid
    ( C ) STRANDEDNESS: single (D) TOPOLOGY: linear (i i) MOLECULE TYPE: DNA (genomic)

(x i) SEQUENCE DESCRIPTION: SEQ ID NO:4:

GCTGGGCATA GAAGTCAG 18

(2) INFORMATION FOR SEQ ID NO:5:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:5:

CTGTGGGGCA AGGTGAA 17

(2) INFORMATION FOR SEQ ID NO:6:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:6:

CTGTGGGGCT AGGTGAA 17

(2) INFORMATION FOR SEQ ID NO:7:

(i) SEQUENCE CHARACTERISTICS:
(A) LENGTH: 19 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:7:

AAGGACTCAA AGAACCTCT 19

(2) INFORMATION FOR SEQ ID NO:8:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:8:

CAGAGGTTGA GTCCTTTG 18

(2) INFORMATION FOR SEQ ID NO:9:

(i) SEQUENCE CHARACTERISTICS:
(A) LENGTH: 27 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:9:

CCATGGCGTT AGTATGAGTG TCGTGCA    27

( 2 ) INFORMATION FOR SEQ ID NO:10:

( i ) SEQUENCE CHARACTERISTICS:
      ( A ) LENGTH: 26 base pairs
      ( B ) TYPE: nucleic acid
      ( C ) STRANDEDNESS: single
      ( D ) TOPOLOGY: linear    ( i i ) MOLECULE TYPE: DNA (genomic)

( x i ) SEQUENCE DESCRIPTION: SEQ ID NO:10:

GATTCCTATG GGAGTGGGCC TCGTCC    26